United States Patent [19]

Kellner

[11] Patent Number: 4,483,197

[45] Date of Patent: Nov. 20, 1984

[54] SOIL STRESS TEST APPARATUS

[75] Inventor: Jordan D. Kellner, Wayland, Mass.

[73] Assignee: The Kendall Company, Boston, Mass.

[21] Appl. No.: 430,535

[22] Filed: Sep. 30, 1982

[51] Int. Cl.³ .............................................. G01B 5/00
[52] U.S. Cl. .................................. 73/784; 73/150 R; 73/432 SD
[58] Field of Search ..................... 73/825, 841, 842, 9, 73/432 SD, 150 R, 150 A, 784

[56] References Cited

U.S. PATENT DOCUMENTS 3,608,367  9/1971  Karol .................................... 73/825
4,304,122 12/1981  Tentor ....................... 73/432 SD X
4,348,206  9/1982  Sandhu ...................... 73/432 SD X

FOREIGN PATENT DOCUMENTS 257823  6/1971  U.S.S.R. ............................... 73/825

Primary Examiner—Gerald Goldberg
Assistant Examiner—E. G. Harding
Attorney, Agent, or Firm—Frederick R. Cantor

[57] ABSTRACT

An apparatus and method is described herein which simulates and applies soil shear stress conditions to test pipe segments and thereby induces the mechanical soil stress effects upon adherent pipeline anti-corrosion protective coatings. A test pipe segment having an adherent anti-corrosion protective coating is emplaced centrally in a test apparatus housing chamber, having both a concentrically-located soil reservoir in contiguous contact with said test pipe segment, and a gas pressure reservoir surrounding said soil reservoir. Desired movements of said test pipe segment are controlled and regulated by a universal testing machine. Gas pressures in the gas pressure reservoir exerts pressure on the soil reservoir, thereby simulating soil stress forces on the centrally disposed pipe segment with its adherent anti-corrosion coating. In addition, the present apparatus and method can readily be used to determine the relative effects of soil shear stress forces on pipeline anti-corrosion coatings as a function of internal pipeline operating temperatures.

27 Claims, 3 Drawing Figures

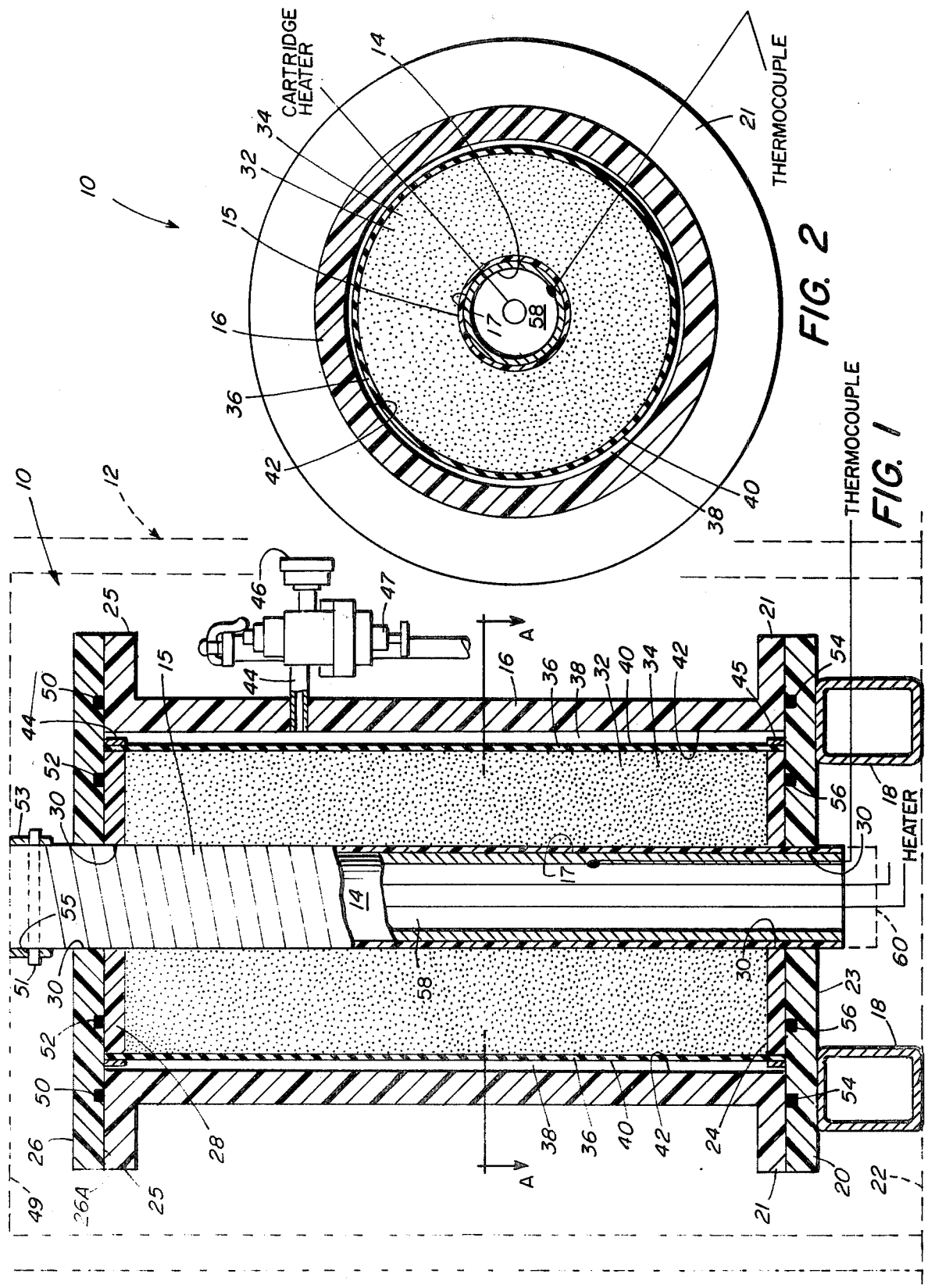

SOIL STRESS TEST APPARATUS

BACKGROUND OF THE INVENTION

The present invention relates to soil stress forces simulating and application devices and methods.

The present invention further relates to devices and methods that both simulate and apply the effects of soil shear stress forces upon test pipe segments and adherent pipeline anti-corrosion protection coatings.

The present invention also relates to devices and methods that both simulate and apply the effects of soil shear stress forces, in combination with the effects of increased internal pipeline operating temperatures upon test pipe segments and adherent pipeline anti-corrosion pipewrap systems.

There exists at the present time an important need for a high soil shear stress-resistant pipeline anti-corrosion system. The widely use pipeline anti-corrosion system usually takes the form of a helically applied tape-like protective outerwrapping. The tape-like component may be applied directly over an unprepared pipeline outer surface, or may, in fact, be overlaid onto a "primer"-coated, pretreated pipeline outer surface.

Other pipeline anti-corrosion protective materials, such as a foam polyurethane material, or the like, may be either sprayed or brushed directly onto a pipeline outer surface prior to inground implantation of the pipe structure.

An important desired characteristic of newly developed pipeline anti-corrosion protective coatings is minimal coating creep in high soil shear stress environments.

In order to attain this coating characteristic, it is deemed extremely important to be able to provide a test apparatus and method that will be capable of both simulating and applying the effects of inground soil shear stress forces upon test pipe segments and adherent pipeline anti-corrosion protective coating systems under pipeline operating temperatures.

Anti-corrosion protective coatings that are to be applied to pipeline structures destined for inground implantation are often subjected to rather severe long-term shearing forces derived from the surrounding soil. The magnitude of these shearing forces depends upon several factors, including amongst others: (a) the type of the soil, (b) the tectonic forces surrounding the implanted pipeline, (c) the size of the pipe, (d) the axial site emplacement and (e) the range of thermal expansion of the pipe as well as its contents under pipeline operating conditions.

In order to understand how each of the above factors affects the overall soil shear stress forces that are imparted to an adherent inground pipeline coating, we first shall consider the forces acting upon implanted pipelines.

Frictional forces acting between the pipeline anti-corrosion protective coating and the surrounding soil are the primary source of soil shear stress. Frictional forces are here defined as the product of the frictional coefficient between the pipeline coating and the soil and the normal force acting around the pipe. As the coefficient of friction depends upon both the nature of the pipeline coating as well as the surrounding soil, it will be found to vary in different applications. Olefin polymer pipeline protective coatings, such as polyethylene, or the like, inherently exhibit lower coefficients of friction, as the proctective tape outer surfaces are smooth and substantially non-adherent.

Other factors having importance in these considerations are the weight of the soil above the pipe, as well as the weight of the pipe, including its contents. In addition, since the normal force will vary depending on the axial position around the pipe diameter, the frictional force, and hence the shearing force, will also be found to vary around the diameter of the pipe.

The result of long-term soil shear forces on a pipeline protective coating is referred to as "soil stress". Soil stress on anti-corrosion protective coatings generally results from the structural shear forces which may also cause the adherent pipeline anti-corrosion protective coating to creep along the pipeline peripheral surface.

Anti-corrosion protective coating creep in these circumstances is, in essence, a long term visco-elastic, or "cold-flow" phenomenon, common to all polymeric substances. The amount of protective coating creep, however, will depend upon the physical properties of the coating. Since the physical properties (i.e. modulus) of the coating, will be temperature dependent, temperature becomes a decisive element in determining the amount of coating creep. At low temperatures, the propensity of the pipeline anti-corrosion protective coating to creep will be substantially reduced, while at elevated temperatures, the likelihood of protective coating creep will be significantly increased, other factors remaining the same.

Previously, it has been necessary to actually field implant large pipeline sections having an anti-corrosion protective coating layer overlaying the outer pipe surface. These implanted test pipe segments are then dug up at desired long time intervals in order to observe the effects of soil stress forces on the anti-corrosion protective coatings.

This prior art ubiquitous method, is clearly a very time-consuming and expensive process, taking from 30 to 90 days, at a minimum to complete, in order to observe the soil stress forces effects on the adherent anti-corrosion protective coatings.

SUMMARY OF THE INVENTION

It is, therefore, an object of the present invention to provide an apparatus and method for simulating and applying the effects of inground soil stress forces, under a wide range of operating temperatures, upon a test pipe segment with an adherent anti-corrosion protective coating.

It is a further object of the instant invention to provide an apparatus and method for testing the effects of simulated soil stress forces on test pipe segments with adherent protective coatings, that is at once simple to use, economic to operate, and free of the prior art limitation requiring long periods of actual pipeline segment soil burial in order to determine the soil stress effects upon the test pipe segments with their adherent anti-corrosion protective coatings.

These and other objects of the present invention are accomplished, in accordance with the illustrated exemplary embodiment of the instant invention, by a soil stress test apparatus and method described herein which simulates and applies soil shear stress conditions to test pipe segments, and thereby induces the mechanical soil stress effects upon adherent pipeline anti-corrosion protective coatings. A test pipe segment having an adherent anti-corrosion protective coating is emplaced centrally in a test apparatus housing chamber, having both a concentrically-located soil reservoir in contiguous contact with said test pipe segment, and a gas pressure reservoir surrounding said soil reservoir. Desired movements of said test pipe segments are controlled and regulated by a universal testing machine. Gas pressures in the gas pressure reservoir exerts pressure on the soil reservoir, thereby simulating soil stress forces on the centrally disposed pipe segment with its adherent anti-corrosion coating. In addition, the present apparatus and method can readily be used to determine the relative effects of soil shear stress forces on pipeline anti-corrosion coatings as a function of internal pipeline operating temperatures.

BRIEF DESCRIPTION OF THE DRAWINGS

In order that the present invention may be more fully and readily understood, and so that further features thereof may be appreciated, the invention will now be described by way of example with reference to the accompanying drawings, in which like reference characters are used throughout to designate like parts, and in which:

FIG. 1 is a vertical cross-sectional view, with some parts shown in elevation, of an exemplary embodiment of the soil stress test apparatus of the present invention.

FIG. 2 is a cross-sectional view taken along line A—A of FIG. 1 of an exemplary embodiment of the soil stress test apparatus of the present invention.

DETAILED DESCRIPTION OF THE PREFERRED EMBODIMENT

Figure 3:
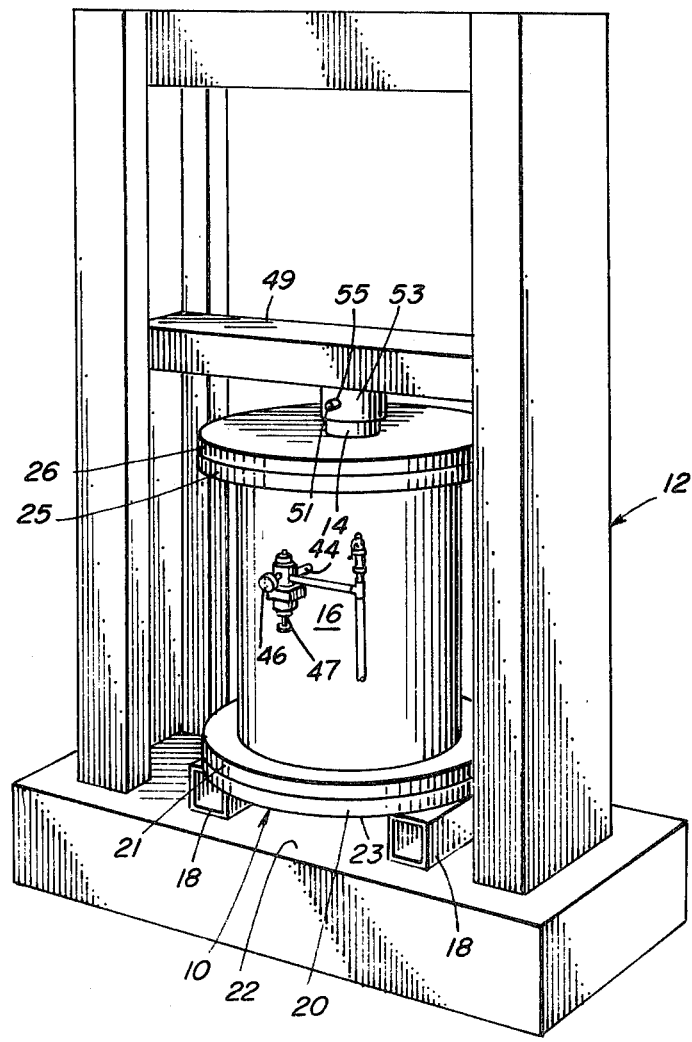
FIG. 3 is a simple perspective view of an exemplary embodiment of the present invention in working position with a universal testing apparatus.

Referring now to FIG. 1, which is a vertical cross-sectional view, with some parts shown in elevation, of an exemplary embodiment of the soil stress test apparatus of the present invention.

As shown in FIG. 1, the soil stress test apparatus of the present invention is depicted generally as 10. The apparatus 10, of the present embodiment is configured as an essentially elongated cylindrical structure. However, other configurations are also possible in other embodiments. It is to be noted that in the preferred embodiment, the apparatus 10 is mounted in close working inter-relationship to an Instron Model 1123, depicted here as 12, or a similar conventional universal testing machine, in order that controlled movements may be imparted to an isolated segment of test pipe during the testing period. These test pipe segment movements will be discussed fully at a later point.

The centrally disposed test segment of pipe, shown in normal testing position in the apparatus 10, and in a connected interrelationship to a universal testing machine 12, is depicted generally as 14. The test pipe segment 14, along with its adherent anti-corrosion protective coating 15, is oriented here vertically, and is centrally-disposed in the test apparatus 10.

The major test cell component housing the soil stress test apparatus 10, is depicted here as 16. The housing 16, of the testing apparatus, encloses the major sub-components of the apparatus 10. The housing 16, as depicted here, is also seen to be essentially an elongated, cylindrically-shaped structure, being composed preferably in the preferred embodiment of a transparent lucite material, or the like.

It is to be also noted that other test cell housing configurations and housing construction materials may also be utilized, if desired, in the design of a particular variant embodiment of the present invention.

Attached to the lower end of the generally cylindrically-shaped housing 16 is a lower outer sealing plate 20. This lower outer sealing plate 20 is attached to a perpendicular lower housing flange 21, preferably by means of bolts (not shown).

Attached to the lower surface 23 of the lower outer sealing plate 20, by means of bolts (not shown), is a pair of suitably spaced housing test cell base mounting blocks 18. These base mounting blocks 18, are essentially hollow, box-like, elongated, preferably metal structures, that allow the test apparatus 10 to be firmly bolted to the table surface 22 of a universal testing machine 12. The suitably spaced orientation, and thickness, of these base mounting blocks 18, also allows a clearance of about 3-4 inches for vertical movement 60, of the test pipe segment 14 during the testing period.

Situated on top of, coplanar with, and in close contiguous contact to the lower outer sealing plate 20, is the lower inner sealing plate 24.

Located at the opposite upper end of the test cell housing 16, is a perpendicular upper housing flange 25, to which is affixed an upper outer sealing plate 26, by bolts (not shown). Situated coplanar to the inner surface, 26A, of the upper outer sealing plate 26, and in close contiguous contact therewith, is an upper inner sealing plate, depicted here as 28.

The four sealing plates, 20, 24, 26, and 28, that are described above, are each essentially disc-like and circular in configuration, with each sealing plate having a centrally-disposed opening 30, therein. These openings, 30, allow for both the alignment of and the extension through the sealing plates, as well as movements 60, vertically and rotationally, of the test pipe segment 14, during the testing phase operation.

It is to be noted that the test pipe segment 14, prior to its emplacement centrally into the test apparatus 10 of the present invention, will typically have an anti-corrosion protective coating, shown here as 15, previously applied to the test pipe segment outer surface 17.

FIG. 1, shows a partially complete vertical cross-section of the test pipe segment 14, with the upper section of the test pipe segment 14, shown not in cross-section, and over-layered with a helically arranged anti-corrosion tape-like coating 15.

FIG. 2 is a cross-sectional view taken along line A—A of FIG. 1 of an exemplary embodiment of the soil stress apparatus of the present invention.

Surrounding the centrally disposed test pipe segment 14, is a contiguously-located, cylindrically-shaped, soil reservoir, depicted herein as 32. Soil material 34 of all types, from finely divided peat or clay particles, to various-sized gravel particles, may be readily utilized in the soil reservoir 32 of the present invention.

These soils, 34, may represent actual samples of soil in the area of intended future pipeline construction.

The soil reservoir 32 is defined by the vertically oriented, centrally-located test pipe segment 14, with its adherent anti-corrosion protective coating 15, by both the lower inner sealing plate 24 and the upper inner sealing plate 28, as well as by a discrete soil reservoir membrane 36.

The soil reservoir membrane 36 is a conformable generally, sheet-like structure, composed of rubber, or the like, that surrounds the soil material 34, located in the soil reservoir 32. Surrounding and contiguous to the soil reservoir membrane 36, in a discrete gas pressure space 38. The gas pressure space 38, is a region located between the outer surface 40 of the soil reservoir membrane 36, and the inner surface 42 of the test cell housing 16.

The gas pressure space 38 is a region that is filled with a gas, such as air, or the like, under pressure and supplied from an external gas supply (not shown) through a gas supply inlet 44, entering the housing 16. A gas pressure regulator valve 47 controls the desired pressure, and a gas pressure gauge 46, indicates the gas pressure contained in the gas pressure space 38.

It is also to be noted that four O-rings, 50, 52, 54, and 56, respectively, which are in contact with both the sealing plates 20, 24, 26, and 28 as well as the flanges 21 and 25 of housing 16, effectively seal from gas pressure leaks, the pressure space 38, located between the soil reservoir membrane outer surface 40, and the inner surface 42 of the housing 16. Pressure clamps, 44 and 45, connect the soil reservoir membrane 36, to both the upper and lower inner sealing plates 28 and 24, also effectively sealing the gas pressure space 38.

The pressure gauge 46 records the gas pressure that is being maintained within the gas pressure chamber 38. The gas pressure in the gas pressure chamber 38, is controlled preferably by a 0–10 psi pressure regulator, 47.

FIG. 3 is a simple perspective view of an exemplary embodiment of the present invention in a working position with a universal testing apparatus.

In the preferred embodiment, a universal testing machine 12, which is capable of compressive and tensile loads, on the order of 5,000 pounds, and having an opening between the outer upright columns of at least 18 inches, is used to obtain the requisite movements 60, of the test pipe segment 14, during the testing period.

As mentioned earlier, an Instron Model 1123, 12, or the like, universal testing machine, is used in the preferred embodiment to control the desired movements of the test pipe segment 14 during the test period. The upper portion of the test pipe segment 14 is readily attached to the crossbar sleeve 53, of the crosshead 49, of the universal testing machine 12, by means of a connecting crosspin 51, said crosspin being also inserted into holes 55, located in the upper end of the test pipe segment 14.

In order to be able to simulate "normal" elevated pipeline operating temperatures during the testing phase of the present method, a cartride-type heater (not shown), is inserted within the interior space 58 of the test pipe segment 14. The cartridge-type heater is controlled by a type J, or the like, thermocouple (not shown), that is inserted underneath the anti-corrosion protective coating 15, surrounding the test pipe segment 14. Insulation, located at the top of the test pipe segment 14, prevents heat damage to a crosshead mounted load cell (not shown).

Following the setting of the desired pipeline operating temperature simulated conditions, the test pipe segment 14 is connected to the universal testing machine 12 through the use of the connecting crosspin 51 located in the holding sleeve 53 of the crosshead 49.

The desired gas pressure is then established by means of gas pressure regulator valve 47. The gas pressure in the gas pressure chamber 38, will result in impingement upon the soil reservoir membrane 36, and thereby its contained soil particles 34. This pressure, in turn, causes a uniformly applied radial pressure to be exerted upon the outer surface of the anti-corrosion protective coating 15, surrounding the centrally-disposed pipe segment 14. The gas pressure that is contained within the pressure chamber 38, and transmitted to the soil reservoir reservoir 34, and thence to the test pipe segment 14, is predetermined, being based upon the actual soil depth that a planned pipeline is to be implanted. Gas pressure established in the gas pressure chamber 38, corresponds to an equivalent of about 0.8 psi for each foot of intended soil depth implantation.

Following the presetting of both the desired simulated internal operating pipeline temperature, as well as the desired gas pressure that will be transmitted to the anti-corrosion protective coating 15 surrounding test pipe segment 14, vertical, and if desired, rotational movements 60, of the test pipe segment 14 in contact with the soil reservoir material 32, is initiated through activation by the universal testing machine 12.

Various test pipe segment 14 movement cycles, varying from between about 0.01 inch/minute for simulating slow creep experiments, up to about 2 inch/minute, may be maintained for the desired test time period. It is also possible to alter the internal pipeline simulated operating temperatures within a wide range from ambient, or below, to 300° C., or more, in order to determine the operating service temperature limits for the anti-corrosion protective coating 15, under study.

Tests with the present invention may be conveniently conducted at generally either six to eight hour intervals, or over 24 hour intervals, or any multiples or fractions thereof. The tests may, in turn, be repeated at progressively higher pipeline internal temperatures, or lower temperatures, if desired, in order to simulate operating and environmental conditions.

The internal pipeline temperature at which the anti-corrosion protective coating damage first appears, indicates the upper operating temperature limits for the subject coating, and in turn, the relative ability of the protective coating to withstand creep and structural damage, generated by simulated soil stress forces. The usefulness of the anti-corrosion protective coating 15 being studied as a corrosion protection barrier, depends upon the ability of the coating to withstand the rigors of soil stress forces during its soil burial.

The useful coefficient of friction (f), may be calculated as follows, for varying anti-corrosion protective coatings using the present invention. The force, F, necessary to either push or pull the test pipe segment 14, with its adherent protective coating 15 through the soil reservoir 34, is measured as a function of the gas pressure on the soil reservoir membrane 36. The total force, R, exerted on the test pipe segment 14, is calculated from the gas pressure and the area of contact. The coefficient of friction, f, is, therefore, easily calculated from: $f = F/R$.

The coefficient of friction is also affected by the nature of the soil as well as by the type of anti-corrosion protective coating overlaying the pipe surface.

The present invention, therefore allows ready determination of the coefficients of friction in various experimental circumstances, thereby allowing for rapid analyses of experimental anti-corrosion coatings in a developmental test program.

The previous detailed description of the preferred embodiment of the present invention is given for purposes of clarity of understanding only, and no unnecessary limitations should be understood or implied therefrom, as such functions and equivalents may be obvious to those skilled in the art pertaining thereto.

What is claimed is:

1. An apparatus for simulating and applying the effects of inground soil stress forces, under varying operating temperatures, upon a movable test pipe segment and adherent protective coating, comprising:
a test apparatus housing means;
an opening for centrally disposing a test pipe segment within said test apparatus housing means;
a test pipe segment movement means;
a soil reservoir located in said test apparatus housing means;
said soil reservoir being in close contiguous contact with and surrounding said test pipe segment;
a soil reservoir containing means;
said soil reservoir containing means surrounding said soil reservoir;
a gas pressure means surrounding said soil reservoir containing means;
said gas pressure means exerting variable gas pressures on said soil reservoir, with induced soil pressure forces in turn being transmitted to said test pipe segment;
said test pipe segment movement means simultaneously providing movement to said test pipe segment during impingement by said soil reservoir.

2. An apparatus for simulating and applying the effects of inground soil stress forces, under varying operating temperatures, upon a movable test pipe segment and adherent protective coating, comprising:
a test apparatus housing means;
an opening for centrally disposing a test pipe segment within said test apparatus housing means;
a test pipe segment movement means; a soil reservoir located in said test apparatus housing means;
said soil reservoir being in close contiguous contact with and surrounding said test pipe segment;
a gas pressure means surrounding said soil reservoir containing means;
said gas pressure means exerting variable gas pressures on said soil reservoir, with induced soil pressure forces in turn being transmitted to said test pipe segment;
said test pipe segment movement means simultaneously providing movement to said test pipe segment during impingement by said soil reservoir.

3. An apparatus for simulating and applying the effects of inground soil stress forces, according to claim 1, wherein said test apparatus housing means is substantially an elongated cylindrical structure.

4. An apparatus for simulating and applying the effects of inground soil stress forces, according to claim 1, wherein the temperature of said test pipe segment is controlled by a temperature control means.

5. An apparatus for simulating and applying the effects of inground soil stress forces, according to claim 4, wherein said temperature control means regulates internal temperature of said test pipe segment.

6. An apparatus for simulating and applying the effects of inground soil stress forces, according to claim 5, wherein said temperature control means simulates internal pipe temperatures in a range from about ambient to about $+300°$ C.

7. An apparatus for simulating and applying the effects of inground soil stress forces, according to claim 1, wherein said test pipe segment moving means is a universal testing machine located in proximity to said test pipe segment.

8. An apparatus for simulating and applying the effects of inground soil stress forces, according to claim 1, wherein said soil reservoir contains soil particles ranging in size from finely divided clay or part to medium size gravel particles.

9. An apparatus for simulating and applying the effects of inground soil stress forces, according to claim 1, wherein soil test pipe segment moving means imparts vertical axial movement in the direction of the test pipe segment in the direction of the long axis of said test pipe segment.

10. An apparatus for simulating and applying the effects of inground soil stress forces, according to claim 1, wherein said test pipe segment moving means imparts rotational movements to said test pipe segment.

11. An apparatus for simulating and applying the effects of inground soil stress forces, according to claim 1, wherein said soil reservoir containing means is a sheet-like conformable membrane.

12. An apparatus for simulating and applying the effects of inground soil stress forces, according to claim 11, wherein said soil reservoir containing means is a rubber composition membrane.

13. An apparatus for simulating and applying the effects of inground soil stress forces, according to claim 11, wherein said soil reservoir containing means is a polymeric membrane.

14. An apparatus for simulating and applying the effects of inground soil stress forces, according to claim 1, wherein said gas pressure means comprises a gas pressure supply means and a gas pressure space.

15. An apparatus for simulating and applying the effects of inground soil stress forces, according to claim 1, wherein said gas pressure is regulated to simulate desired soil depth soil stress forces on implanted test pipe segment and adherent protecting coating.

16. A method of simulating and applying the effects of inground soil stress forces, under varying operating temperatures, upon a movable test pipe segment and adherent protective coating, comprising the steps of:
emplacing in a test apparatus housing means said test pipe segment;
surrounding in close contiguous contact said test pipe segment with a contained soil reservoir;
incorporating gas into a gas pressure space;
said gas pressure space surrounding said contained soil reservoir;
said gas pressure in said gas pressure space impinging upon said soil reservoir;
said soil reservoir thereby impacting upon said test pipe segment and adherent protective coating; and
simultaneously applying movements to said test pipe segment with a test pipe segment movement means.

17. A method of simulating and applying the effects of inground soil stress forces, according to claim 16, wherein said test apparatus housing means is an essentially elongated cylindrical structure.

18. A method of simulating and applying the effects of inground soil stress forces, according to claim 16, wherein a temperature control means regulates internal temperatures of said test pipe segment.

19. A method of simulating and applying the effects of inground soil stress forces, according to claim 18, wherein said temperature control means simulates and regulates internal pipe temperatures in a range from about ambient temperature to about $+300°$ C.

20. A method of simulating and applying the effects of inground soil stress forces, according to claim 16, wherein said test pipe segment moving means is a universal testing machine located in proximity to said test pipe segment.

21. A method of simulating and applying the effects of ingrond soil stress forces, according to claim 16, wherein said soil reservoir contains soil particles ranging in size from finely divided clay or peat to medium-size gravel particles.

22. A method of simulating and applying the effects of inground soil stress forces, according to claim 16, wherein said test pipe segment moving means imparts vertical axial movements to the test pipe segment, in the direction of the long axis of said test pipe segment.

23. A method of simulating and applying the effects of inground soil stress forces, according to claim 16, wherein said test pipe segment moving means imparts rotational movements to said test pipe segment.

24. A method of simulating and applying the effects of inground soil stress forces, according to claim 16, wherein said contained soil reservoir means is surrounded by a sheet-like membrane.

25. A method of simulating and applying the effects of inground soil stress forces, according to claim 24, wherein said soil reservoir containing means is a rubber composition membrane.

26. A method of simulating and applying the effects of inground soil stress forces, according to claim 24, wherein said soil reservoir containing means is a polymeric membrane.

27. A method of simulating and applying the effects of inground soil stress forces, according to claim 16, wherein said gas pressure is regulated to simulate desired soil depth soil stress force on implanted test pipe segment and adherent protective coating.

* * * * *